United States Patent
Bisconte Sconte De Saint Julien

Patent Number: 6,143,577
Date of Patent: Nov. 7, 2000

[54] PROCESS AND INSTALLATIONS FOR SEPARATION OF MAGNETIC PARTICLES IN A FLUID FOR BIOLOGICAL ANALYSIS, AND APPLICATION OF SAID PROCESS

[75] Inventor: Jean-Claude Bisconte Sconte De Saint Julien, Briis sous Forges, France

[73] Assignee: Biocom S.A., Le Sulis, France

[21] Appl. No.: 08/952,493

[22] PCT Filed: May 5, 1997

[86] PCT No.: PCT/FR97/00794

§ 371 Date: May 15, 1998

§ 102(e) Date: May 15, 1998

[87] PCT Pub. No.: WO97/42503

PCT Pub. Date: Nov. 13, 1997

[30] Foreign Application Priority Data

May 7, 1996 [FR] France .................................. 96 05727

[51] Int. Cl.$^7$ ...................... G01N 33/553; G01N 33/537; B01D 35/06

[52] U.S. Cl. .......................... 436/526; 436/149; 436/531; 436/534; 436/806; 436/810; 436/528; 436/807; 436/824; 435/7.2; 435/7.21; 435/7.23; 435/7.25; 435/7.32; 435/7.34; 435/7.92; 435/7.93; 435/971; 435/7.94; 435/7.95; 210/222; 210/223; 210/695

[58] Field of Search ..................... 436/526, 149, 436/806, 810, 531, 534, 807, 824, 528; 435/7.2, 7.21, 7.23, 7.25, 7.32, 7.34, 7.92, 7.93, 7.94, 7.95, 971; 210/222, 695, 223

[56] References Cited

U.S. PATENT DOCUMENTS

| | | | |
|---|---|---|---|
| 4,239,494 | 12/1980 | Clements | 23/230 |
| 4,438,068 | 3/1984 | Forrest | 422/61 |
| 4,738,773 | 4/1988 | Moiller-Ruchholtz et al. | 209/214 |
| 4,816,143 | 3/1989 | Vollmar | 209/212 |
| 5,186,827 | 2/1993 | Liberti et al. | 210/222 |
| 5,466,574 | 11/1995 | Liberti et al. | 435/5 |
| 5,536,644 | 7/1996 | Ullman et al. | 435/7.25 |
| 5,541,072 | 7/1996 | Wang et al. | 422/58 |
| 5,736,413 | 4/1998 | Uzan et al. | 436/526 |
| 5,834,197 | 11/1998 | Parton | 435/6 |
| 5,837,144 | 11/1998 | Bienhaus et al. | 210/222 |

Primary Examiner—Christopher L. Chin
Assistant Examiner—Pensee T. Do
Attorney, Agent, or Firm—Oblon, Spivak, McClelland, Maier & Neustadt, P.C.

[57] ABSTRACT

A process for magnetic immunoseparation of cells, in particular bacteria, fetal cells, stock cells of bone marrow and circulating cancerous cells, of the type consisting in affixing the target cells on paramagnetic balls and in causing a magnetic field to act on a sample containing the affixed cells, the free cells and the surplus paramagnetic balls, in order to isolate the paramagnetic balls, in that the sample is caused to circulate in a tube the section of which is much less than the length over which the magnetic field is applied.

14 Claims, 7 Drawing Sheets

PROCESS AND INSTALLATIONS FOR SEPARATION OF MAGNETIC PARTICLES IN A FLUID FOR BIOLOGICAL ANALYSIS, AND APPLICATION OF SAID PROCESS

BACKGROUND OF THE INVENTION

1. Field of the Invention

This invention relates to a process and an installation for separation of magnetic particles in a fluid for biological analysis of rare occurrences.

2. Discussion of the Background

The invention finds its application more specifically in the areas of medical diagnosis and quality control particularly in the agro-foodstuffs industry, but also in the therapeutic area in order to detect and extract a cell type with low occurrence in samples.

There may be cited by way of examples of medical applications of the invention:

The separation of fetal cells occurring in the maternal blood. In this case, it involves selectively collecting cells occurring in a ratio of approximately 1 fetal cell to 10 million non-fetal cells. The use of this invention should make it possible to replace the risky extractions of amniotic cells.

The preparation of stock cells of bone marrow, making it possible to resow marrow destroyed following anti-cancer treatment by chemotherapy or radiotherapy. As in the case of fetal cells, the number of bone-marrow cells in the peripheral blood is far below that of other cells, on the order of 1 to 200,000.

The early detection of circulating cancerous cells or micrometastasis, which is of the greatest value for determining exploratory and therapeutic strategies. There again, the objective is to isolate and identify 1 cell in approximately 5 million nucleate cells.

In the area of biological monitoring of foods or the environment, the objective is to obtain a rapid result without going through the conventional phase of propagation in a culture. The expected sensitivities are on the order of 1 cell (bacterium, yeast or mold) to 1 gram or even 10 grams of product. In the prior art there are many devices making it possible to reach this goal. Among the latter may be cited:

Physical methods based on differences of size, density or electrical charge (De Duve, 1971; Zeiller, 1972; Pretlow and Pretlow, 1982). But these methods show a lack of specificity.

Immuno-affinity methods consisting in affixing an antibody on a carrier, which antibody reacts with respect to an antigenic motif present on the surface of the cells sought (Forsgren and Sjoquist, 1986; Langone, 1982). Various processes deriving from the immuno-affinity methods, such as affinity chromatography (Hunt et al., 1982), have been proposed.

Cellular separation combined with a fluorescence detection deriving from the so-called "FACS" method for the English term "Fluorescence Activated Cell Sorting." This widely described method makes use of sophisticated equipment comprising a liquid flux in which the cells move. A laser beam stimulates the fluorescence and thus sets off a signal which makes it possible to divert the cell electrically into a container. This method if very effective and makes it possible to achieve an enrichment of nearly 100%, but it is not suitable for the sorting of large populations.

The magnetic separation methods designated as "MACS" for the English term "Magnetic Affinity Cell Sorting," which is based on the use of magnetic particles ingested by the cells (Melville et al., 1975) or selectively affixed to the cells through the expedient of antibodies (Molday et al., 1977).

The FACS and MACS methods are well known nowadays and already have resulted in an industrial implementation. Generally speaking, the results obtained with each of these methods differ little in terms of efficacy and make possible between 70 and 100% recovery. Nonetheless, they are more or less suitable to the various applications contemplated.

SUMMARY OF THE INVENTION

This invention also is based on the use of magnetic particles on the surface of which is fixed a substance capable of binding specifically to a complementary substance which is free or present on the surface of the cells. The analysis is performed in a liquid medium by subjecting the biological medium into which said magnetic particles were introduced to a magnetic field.

The magnetic particles more specifically contemplated in the context of the invention are microballs of the type marketed by the Dynal, Rhône Poulenc or Sigma companies.

These paramagnetic microballs of micronic size may comprise different ligands on their surface according to the application which is contemplated. These ligands are affixed to the surface of the microballs by the techniques described in the prior art, which ligands may be:

Specific poly- or monoclonal antibodies for antigens present on the surface of certain cellular types, such as CD2, CD4, CD8 proteins expressed on the surface of T lymphocytes. These antibodies are affixed to the surface of the microballs, for example by the expedient of immunoglobulins.

Oligonucleotides, for example oligo(dT) or oligo(dA) of variable sizes, biotinylated and thus affixed to the surface of the microballs by the expedient of streptavidin. These oligonucleotides make it possible through hybridization to purify or extract RNA or DNA from previously-treated samples in order to make the nucleic acids which it contains suitable to be hybridized. The use of these oligonucleotides affixed to the surface of paramagnetic balls also may constitute a preparatory phase for a protocol for amplification through PCR or a cloning after PCR, or even be used for a solid-phase sequencing.

The balls thus charged with a ligand are placed in contact with the sample possibly having undergone a preliminary treatment, so as to achieve the isolation of the sought occurrence through the action of a magnetic field.

But the use of this technique has the drawback of requiring multiple manipulations and leads to a group of balls more or less aggregated by the action of the magnet, among which are some rare cells. The disproportion of the number of balls with respect to the number of cells, on the order of 1 to 10, then makes the identification and collection of these cells impossible. Various solutions to eliminate these drawbacks are proposed in the prior art, such as the action of a detergent, which release the cellular nuclei but subsequently preclude the use or identification, visually or through an antibody, of the separated cells, or else the use of detaching products which act in a variable manner.

Now, in certain cases, the vital nature of the separated cells is of prime importance, either because it is planned to reuse the cells therapeutically, as in the case of hematopoietic stock cells, or to put them back in in-vitro cellular culture in order to amplify a signal, as in the case of fetal cells. The conventional techniques making use of the microballs described above then may have an injurious effect on the cells and prevent the use of separator columns, subjecting the cells to a complicated and traumatizing course.

The state-of-the-art processes therefore are not completely satisfactory. In particular, artifacts reduce the theoretically foreseeable performances. In fact, the surplus paramagnetic balls sometimes have a tendency to form a matrix completely confining a target cell. Considering the very low occurrence of the target cells, this phenomenon is particularly distressing.

Moreover, the separation operations require scrupulous adherence to a tedious and repetitive protocol, which is a source of error.

The purpose of this invention, therefore, is to afford a process omitting the stages of rinsing and elimination of the cells and liquids not sought, and at the same time automatic selection of the sought elements and isolation from the free paramagnetic balls.

Another purpose of this invention is to improve the efficacy of the magnetic processes by avoiding the artifacts noted in the processes of the prior art and by simplifying the working protocol.

It has as a purpose to facilitate separation with a view to counting, analysis or treatment of the biological material present in very low concentrations in a sample. The sensitivities sought in the areas referred to above can be on the order of 1 cell to 1 or even 10 gram(s) of sample.

European patent EP206077 also is known in the state of the art.

This patent teaches the general principle of magnetic immunoseparation by circulation in a tubular segment placed in a uniform magnetic field. It became evident in certain instances of use that the surplus particles could be attracted too rapidly at the beginning of the tube, and that agglomerates were created, blocking the circulation of the marked or unmarked cells. Considering the rarity of the target cells, this situation is very problematic. The invention seeks to remedy this drawback by proposing to create a nonhomogeneous magnetic field. This feature prevents the formation of agglomerates of unaffixed particles in the upper portion of the tubular segment. The application of a nonhomogeneous magnetic field combined with the flux produced by the flow of the sample in the tube with a section which is small in comparison with the length leads to a better distribution of particles and facilitates the release of the agglomerates through the effect of carrying along of the free or affixed cells with larger dimensions. These cells exert a slight pressure on the agglomerates of magnetic particles, which are released in the weak-field zones to become reaffixed in an isolated manner and no longer agglomerated in the next strong-field zone.

These objectives are achieved by virtue of a process and an installation combining, after placement in contact of the sample and the balls, flux and magnetic separation at one and the same time.

To this end, the invention relates first of all to a process for magnetic separation of cells, in particular bacteria, fetal cells, stock cells of bone marrow and circulating cancer cells, of the type consisting in affixing the target cells on paramagnetic balls and causing a magnetic field to act on a sample containing the affixed cells, the free cells and the surplus paramagnetic balls, in order to isolate the paramagnetic balls, characterized in that the sample is caused to circulate in a tube the section of which is much less than the length over which the magnetic field is applied.

The sample preferably flows at a speed of a few centimeters per second. The surplus balls, by reason of their density lower than that of the marked or unmarked cells, or the mass of paramagnetic balls, because of their strong sensitivity to the magnetic field, are drawn rapidly against the wall of the tube and are immobilized in the proximal portion of the tube.

The unaffixed cells are insensitive to the magnetic field and pass through the tube. The cells affixed on the paramagnetic balls are carried along by the flux to the interior of the tube, before being immobilized against the wall of the tube, in the distal portion of the tube.

A geometric separation of the components of the sample thus is undertaken, which makes possible a recovery of the target cells by various means which are simple to implement.

According to one preferred embodiment, the sample is caused to circulate in a tube coiled in a spiral placed in a magnetic field the lines of flux of which are appreciable perpendicular to the plane of the spiral.

The section of the tube advantageously ranges between 0.5 and 3 millimeters and the length of the tube is in excess of 10 centimeters.

The tube preferably is placed in a nonhomogeneous magnetic field. This field may be produced by a permanent magnet or by an electromagnet.

According to an advantageous variant, the preparation is introduced into a reservoir connected to the separation tube, said reservoir being raised in relation to the tube in order to ensure a circulation of the sample by gravity.

The invention also relates to an installation for magnetic immunoseparation of cells, in particular bacteria, fetal cells, stock cells of bone marrow and circulating cancerous cells, characterized in that it consists of a tube the section of which is much smaller than the length, said tube being coiled to form a spiral, and at least one magnet arranged so as to create a magnetic field appreciably perpendicular to the plane of the spiral formed by said tube.

According to a specific embodiment, it comprises a tube having two increasing-section ends, the second section being at least 10 times greater than the first section.

The invention also relates to the applications of this process for:

immunofiltration of blood in extracorporeal circulation prenatal diagnosis biological analysis in the laboratory.

BRIEF DESCRIPTION OF THE DRAWINGS

The invention will be understood better upon reading of the following, making reference to the attached drawings relating to the non-limiting examples of embodiment, where.

DISCUSSION OF THE PREFERRED EMBODIMENTS

Figure 1A:
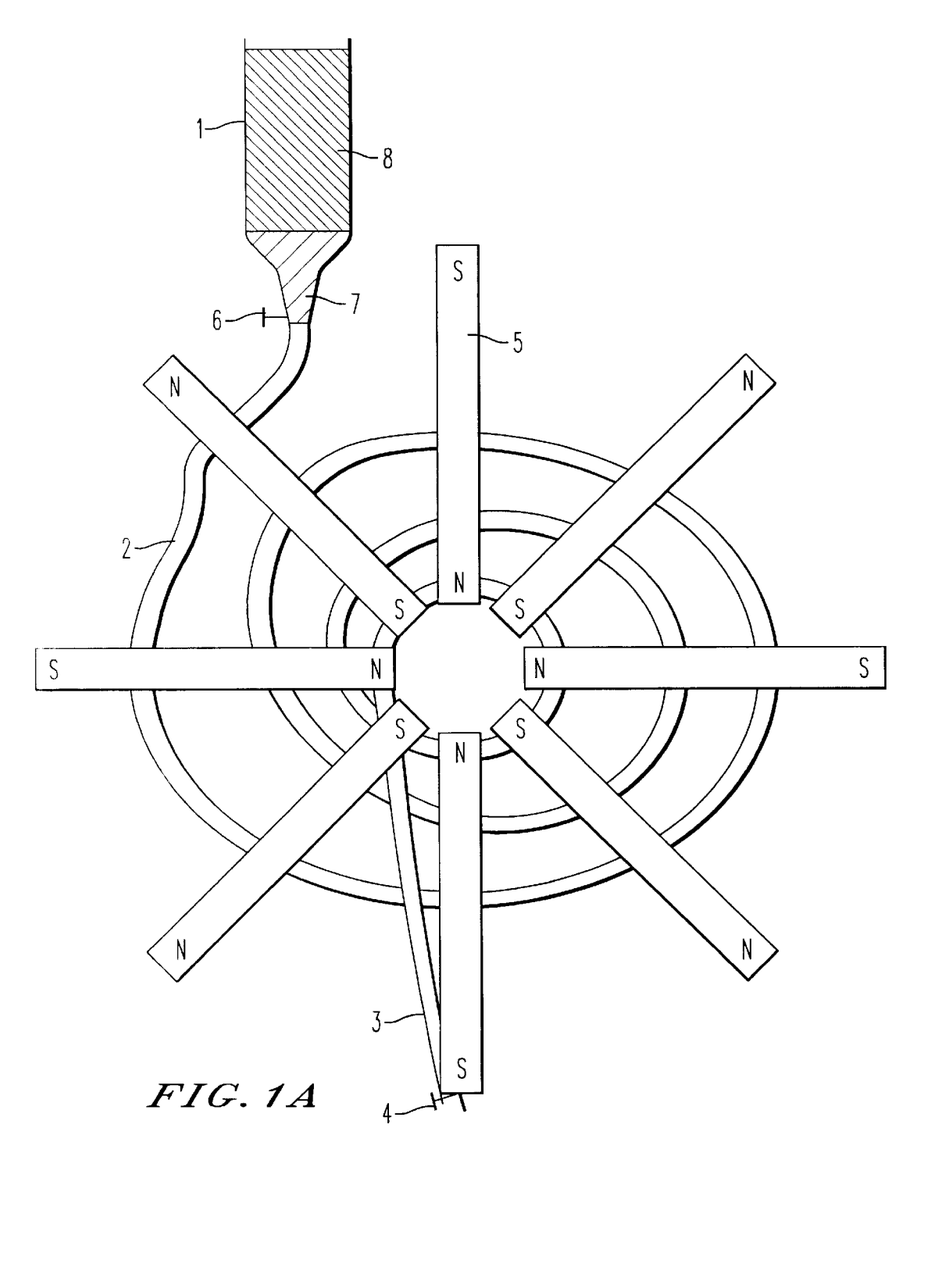
FIG. 1A depicts a front view of an apparatus according to the invention.

FIG. 1A depicts a front view of an example of embodiment of an apparatus according to the invention. It is composed of a container (1) capable of holding approximately 10 to 50 milliliters, connected to a tubulure (2) coiled into a spiral and terminating in an outlet tubulure (3) equipped with a valve (4). A set of permanent magnets (5) is arranged radially in order to create a nonhomogeneous magnetic field. The arrangement of the magnets is shown by way of example, a different arrangement, for example in the form of parallel magnets, also being applicable. The magnets (5) consist of samarium-cobalt bars. These bars possibly may be mounted on a rotating holder disk. This variant makes it possible at one stage of the process to carry the affixed paramagnetic balls along toward the outlet of the tubulure. By way of example, they rotate alternately at ±20°. The maximum speed of carrying along is a few millimeters per second, so as to optimize the effectiveness on the paramagnetic particles.

Different methods of carrying along by the magnets may be provided for:

If the movement occurs continuously in the direction of the flow, removal of the cells and particles will be facilitated;

If the movement occurs continuously in a direction opposite to the flow, removal of the cells and particles will be delayed;

If the movement is alternating, a stirring of the particles will be effected, facilitating rinsing and elimination of the cells and particles.

The section of the tubulure (2) is approximately 0.5 millimeters. It is made of a material such as TEFLON (registered trademark). The length is approximately 50 centimeters.

Use of the apparatus is as follows:
a) to begin with, a rinse liquid of the PBS (trade name) type is introduced into a 20-milliliter pipette;
b) the sample of blood (7), which was incubated beforehand with paramagnetic particles, is aspirated. Nine millimeters of physiological serum (8) are added;
c) the container (1) is connected to the spiral tubulure (2), scrupulously avoiding the formation of bubbles;
d) the container (1) is raised approximately 30 centimeters in relation to the spiral;
e) the valve (6) provided between the container (1) and the tubulure (2) is opened. The liquids then flow continuously from the container (1) toward the spiral tubulure (2) under the effect of hydrostatic pressure.
f) the flow is halted after having allowed half of the 20 milliliters of rinse liquid to go through. During this phase, the effectiveness of the rinse may be increased by causing the magnets (5) to rotate in alternating manner, for example by repeating 5 times a cycle of 20° movement in the trigonometric direction, then return to the initial position, then 20° in the antitrigonometric direction.

The following stage consists in the recovery of the rosettes or nuclei of the sought cells.

1) Recovery of the Rosettes

The spiral (2) is moved away from the effect of the magnetic bars (5), and the flow of the remaining rinse liquid is resumed. The latter is going to carry along all the paramagnetic particles and the cells bearing paramagnetic particles. The sought particles thus could be recovered by filtering, with the aid of a filter permitting the paramagnetic particles, but not the cells, to pass through.

2) Recovery of the Nuclei of the Sought Cells.

To recover the nuclei of the cells, the magnetic effect will be maintained and a new reagent, which will have the feature of lysing the affixed cells by releasing the hardened, stained nuclei, will be caused to act. By way of example, such a reagent consists of the following mixture:

Detergent, for example CETRIMIDE (trade name)
Fixative, for example formaldehyde
Nuclear stain, for example propidium iodide.

This mixture is introduced into the container (1) so that the volume does not exceed that of the spiral (2). The staining facilitates visualization of the advance of the liquid. This mixture is left in contact with the spiral for 10 minutes. The magnets are activated in alternating movements in order to facilitate the release of the nuclei. Then rinsing may be performed to recover the pure nuclei. The magnets (5) always being present, no magnetic particle will contaminate the preparation. On the other hand, the cells being destroyed, identification of the nuclei involves the use of molecular hybridization reagents. The latter make it possible to detect genetic anomalies such as the presence of a supernumerary centromere (trisomy 21) or amplified expressions of oncogenes, or even expressions of specific P53-type genes. Moreover, the pure nuclei stained in stoichiometric manner make it possible to define a ploidy level which characterizes the stages of tumorous cells.

Figure 1B:
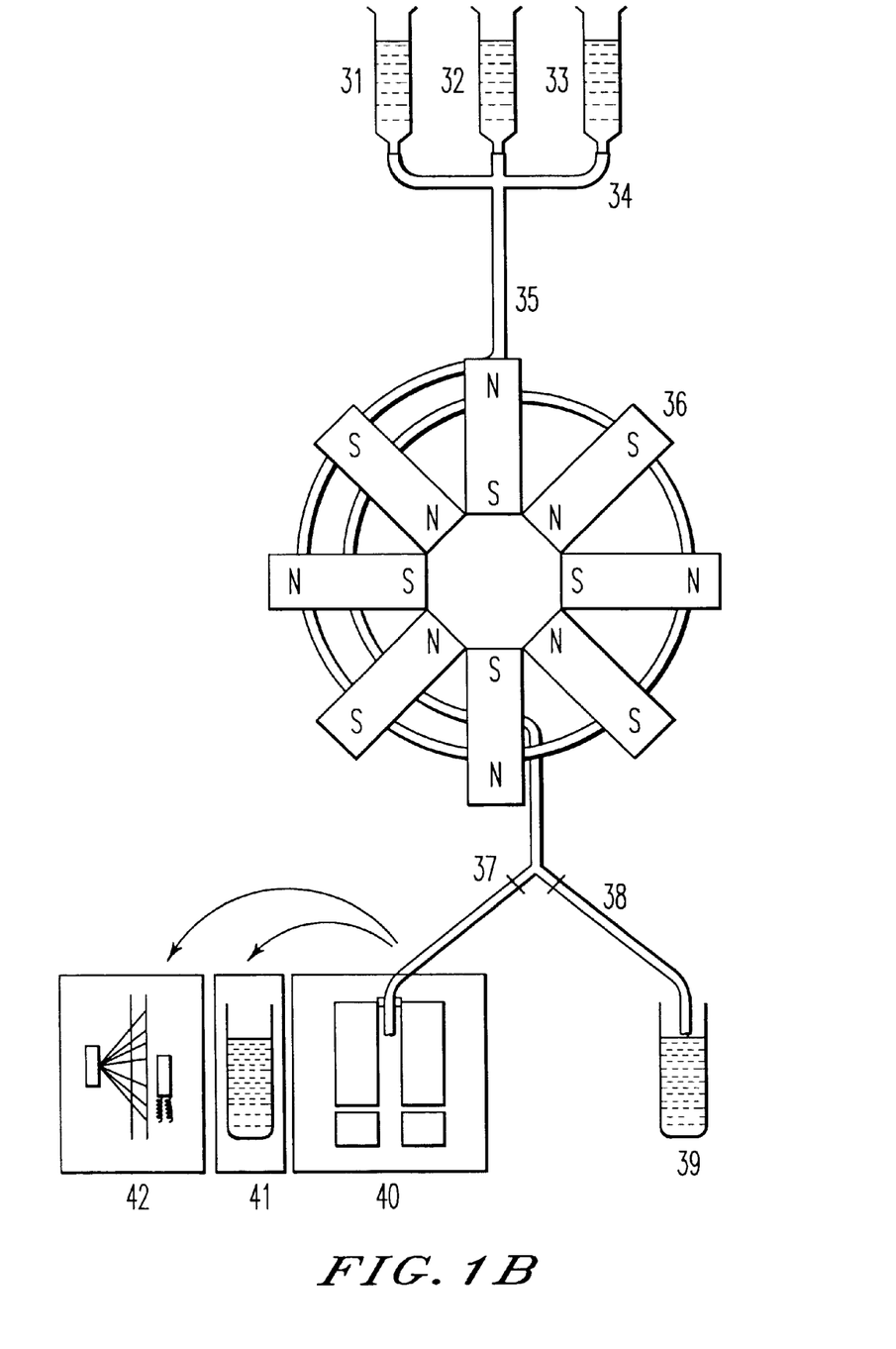
FIG. 1B depicts a front view of an apparatus according to the invention.

FIG. 1B shows a variant of embodiment of an apparatus according to the invention. The apparatus comprises three containers (31 to 33) of reagents and samples connected to a separator pipe (35) coiled in a spiral. Automatic spigots or valves turn on or turn off the flow from each of the containers (31 to 33) toward the separator pipe (35). This separator pipe is positioned in a magnetic-field gradient generated by permanent magnets (36) arranged in a star pattern, in alternating radial direction. The lower end of the separator pipe (35) opens on the one hand into a collection pipe (37) and on the other into a removal pipe (38). Valves or spigots are provided on each of these pipes to direct the flow toward a rejection container (39), or toward analysis means formed by a system of collection on a filter (40), a collection container (41) or a particle flux detector (42).

Figure 2:
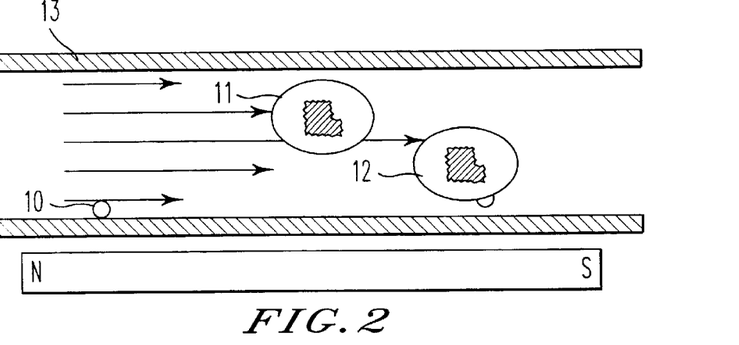
FIG. 2 depicts a cross-section of the tubulure.

FIG. 2 depicts a cross-section of a segment of tubulure. Under the effect of Bernouilli's forces, the particles have a tendency to become concentrated in the center of the flux, where the speed is greatest. Under the effect of magnetic fluxes, the paramagnetic balls (10), lighter and less voluminous than the unmarked particles (11) and the marked cells (12), are drawn very rapidly toward the wall (13) of the tubulure.

The trajectory of the unmarked cells (11) is not disturbed by the magnetic fluxes and they therefore remain in the center of the flux where they are rapidly carried along toward the outlet.

The marked cells (12) are found in the last portion of the tubulure (2). The tubulure possibly may be implemented with two segments with increasing section, the first serving to retain the surplus balls, and the second to retain the marked cells.

Figure 3:
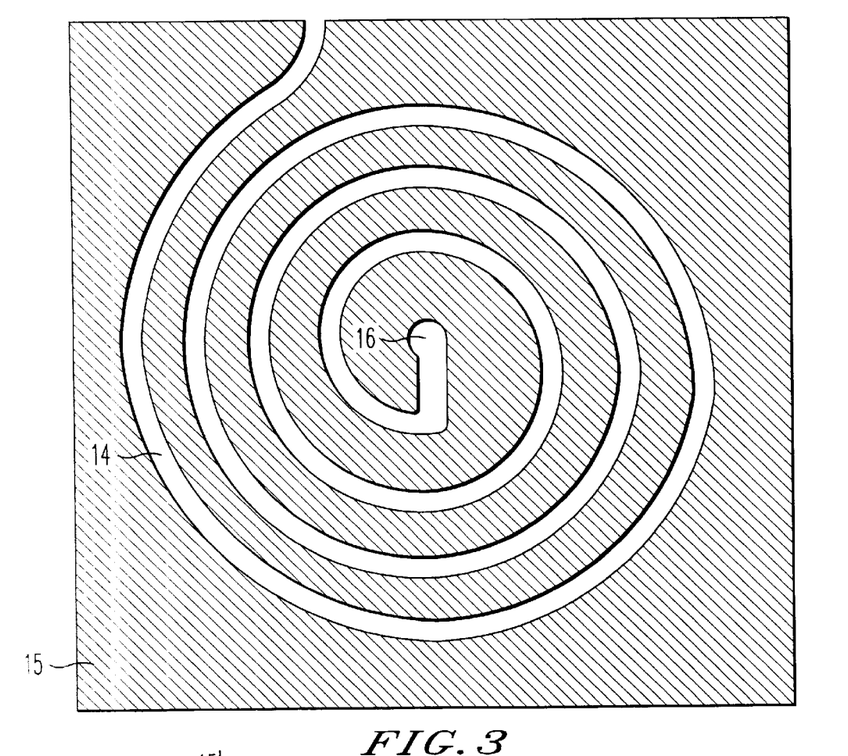
FIG. 3 depicts a view of a variant of embodiment.
Figure 4:
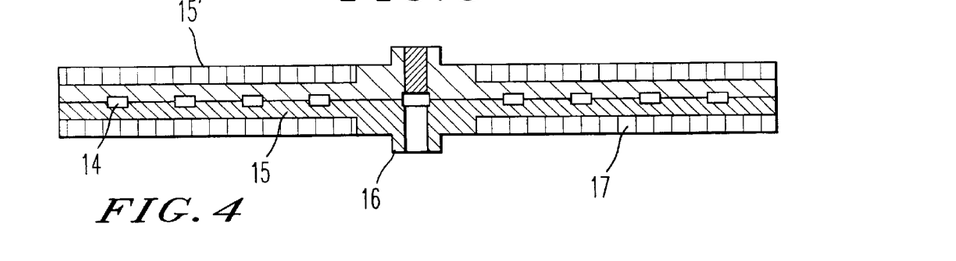
FIG. 4 depicts a transverse cross-section of a variant of embodiment.

FIGS. 3 and 4 depict median-section and cross-section views, respectively, of a variant of embodiment.

The tubulure (2) is formed by a groove (14) executed in a plastic plate (15). It opens on the one hand onto one of the lateral edges in order to allow connection to a tubulure for joining with the feed container (1), and on the other with a transverse orifice (16) traversing the plate (15) allowing removal of the fluids. The apparatus is made up of two symmetrical plates (15, 15') and are connected in such manner as to define between them the tubulure for circulation of the liquid. On the outer surfaces they provide housings for the magnets (17).

Figure 5:
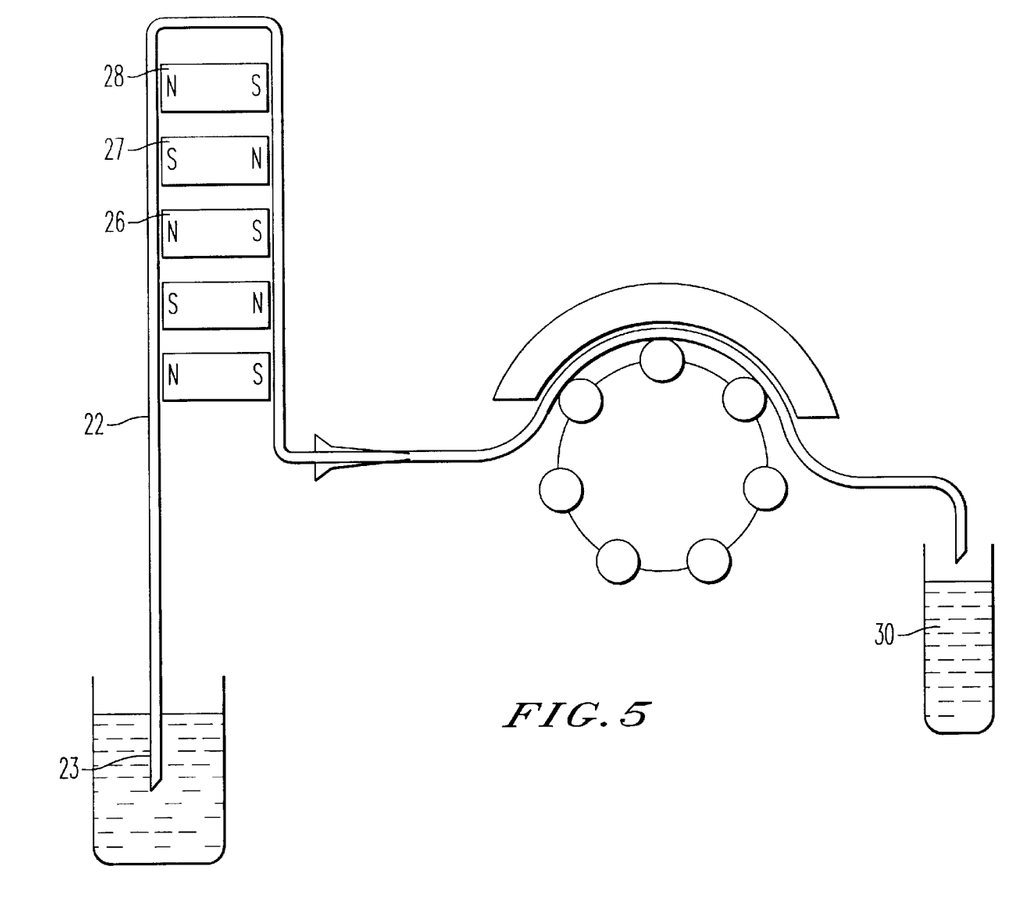
FIG. 5 depicts a view of a second variant of embodiment using a peristatic [sic] pump.

FIG. 5 depicts a view of a second variant of embodiment using a peristatic [sic] pump. In this variant, the advance of the liquids is not influenced by gravity, but by a peristatic [sic] pump.

The apparatus consists of a tubular element (22) forming a separating loop. One of the ends aspirates the treated sample as in the preceding examples. The tubular element (22) is arranged in the field of permanent magnets (24 to 28) oriented perpendicularly to the course of movement of the liquid, in alternating directions. The tubular element (22) is disposable, which avoids any contamination of its inner walls.

This tubular element (22) is connected to the aspiration tube of a peristaltic pump (29) of known type. The wastes are collected in a test tube (30) at the outlet of the pump (29). Circulation of the fluid inside the tube preferably is continuous, with a speed on the order of 1 cm per second. The continuous circulation avoids formation of cellular adhesions on the wall of the separation tube.

Figure 6A:
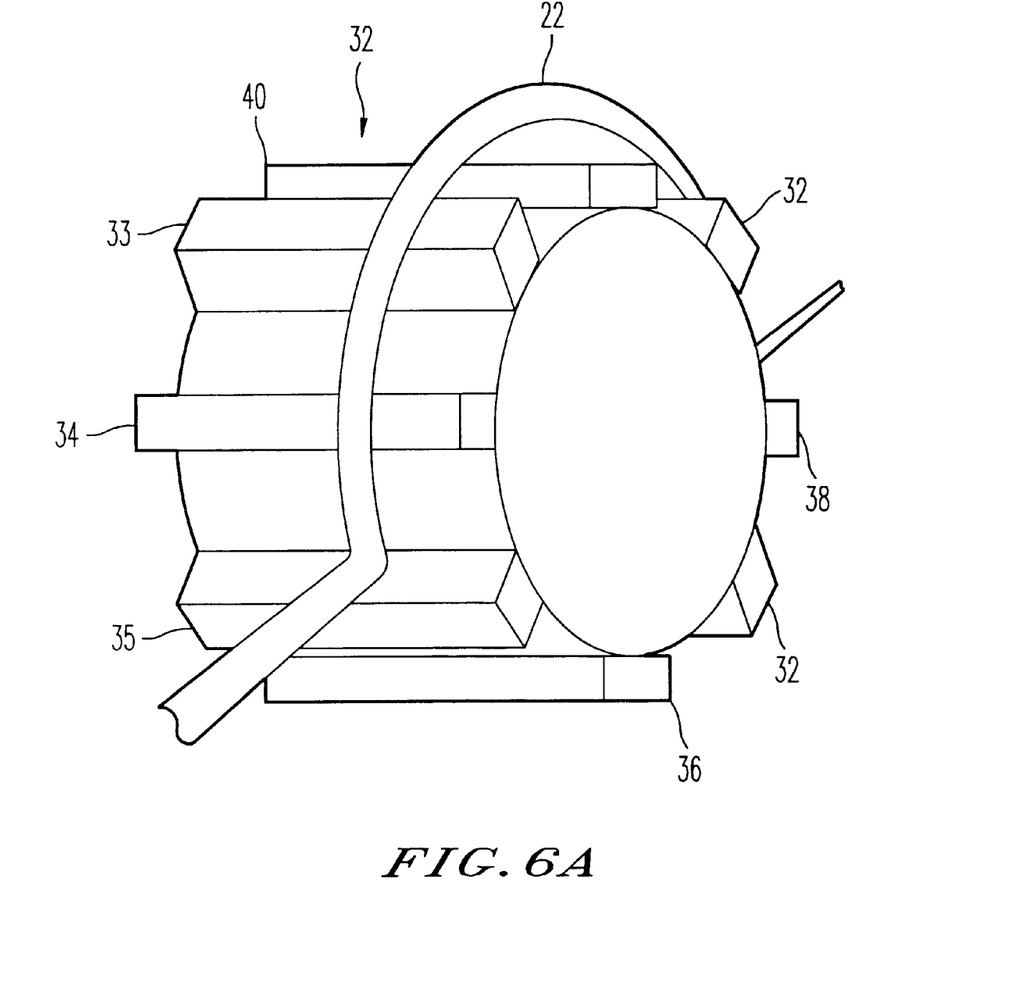
FIG. 6A depicts a view of another variant of embodiment using a peristaltic [sic] pump.
Figure 6B:
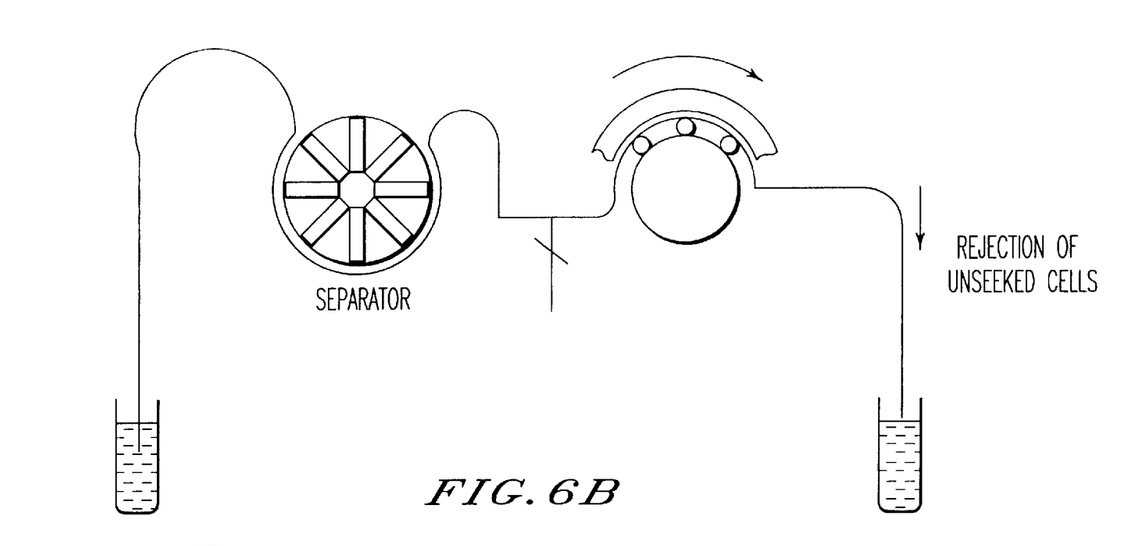
FIG. 6B depicts a view of another variant or embodiment using a peristatic [sic] pump.
Figure 6C:
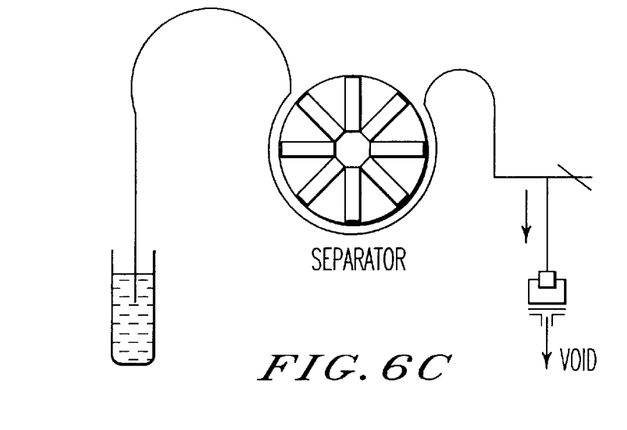
FIG. 6C depicts a view of another variant of embodiment using a peristatic [sic] pump.

FIGS. 6A, 6B and 6C depict a partial view of a variant of embodiment. The magnets form a squirrel cage (32) consisting of a number of magnetic bars (33 to 40) magnetized radially in an alternating direction. This structure makes it possible to position one or several tubular elements (22), and to treat several samples in parallel.

The use of such an apparatus is as follows:

The free end (23) of the separator pipe (22) is immersed in the sample which received the paramagnetic particles beforehand.

The pump (29), which is going to cause the magnetic particles and the cells to pass into the separating loop arranged in the magnetic field, is activated. The magnetic particles and the rosettes formed by the marked cells are going to come to a halt in this loop, while the other cells are going to be removed. Thus in order to undertake a cellular purge, in particular for a therapeutic purpose, consisting in eliminating the marked cells so as to collect only the unmarked cells, it is preferable to replace the peristaltic pump with another means of aspiration, for example an aspirating syringe or a depression source, in order to avoid crushing of the unmarked cells.

This embodiment offers several advantages:
  it makes it possible to treat a large number of samples in parallel,
  it makes it possible to automate the handling of the stages,
  it makes it possible to treat very large volumes,
  it avoids dead capacity above the treatment zone in the tubular element. In fact, after the passage of the sample, the tube may be eliminated is [sic; intended word and] the reagents conveyed from uncontaminated containers. The risk of recovering non-specific cells is greatly reduced. In addition, all the pipes then may be immersed in the same reagent container, which simplifies manipulations.

Figure 7:
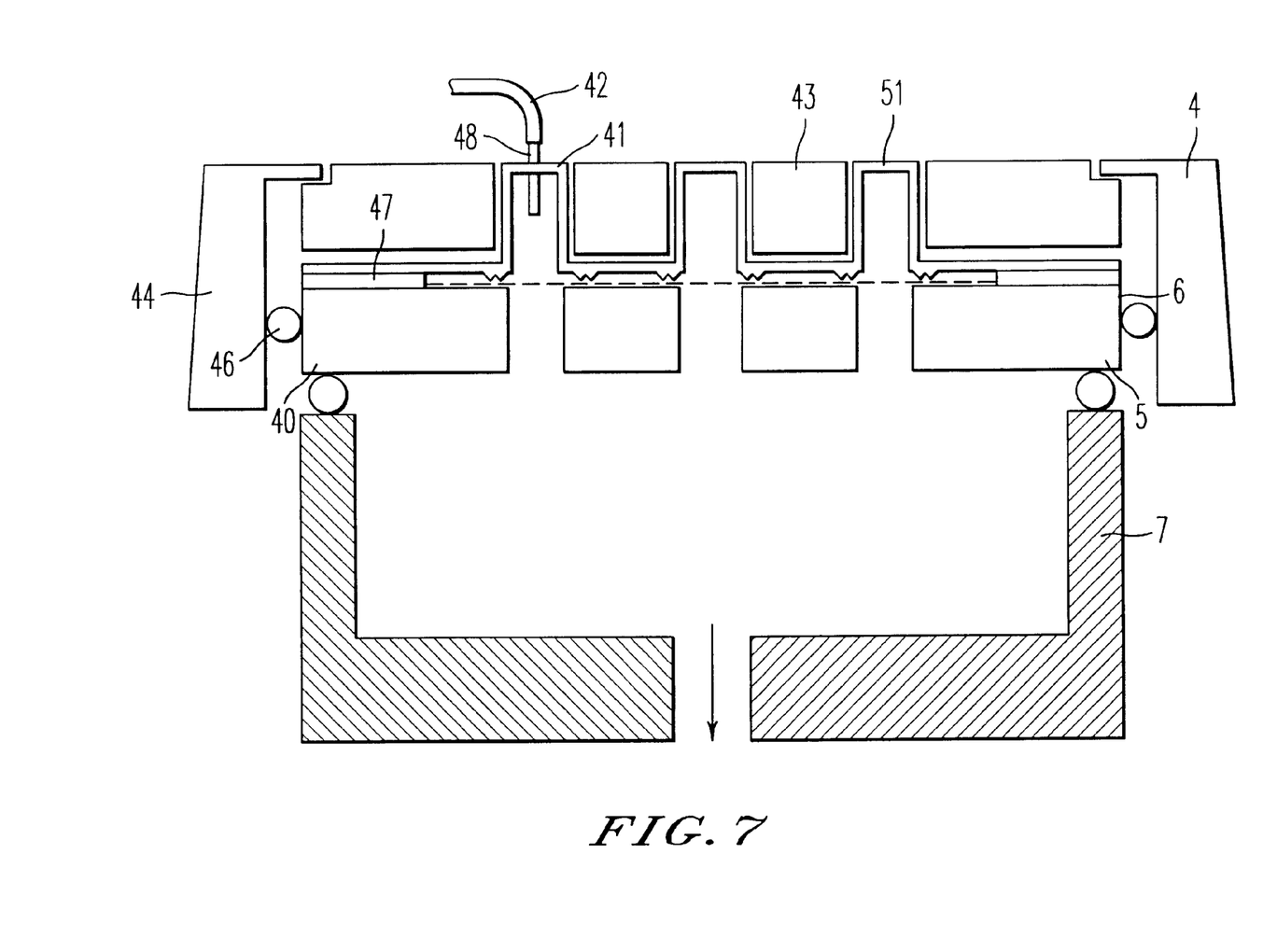
FIG. 7 depicts a cross-section of a filtration module for separation of the magnetic particles.

The separation of the marked cells and the unaffixed magnetic particles after the use of a treatment system according to one of the preceding variants advantageously is performed by means of a filtration apparatus, an embodiment example of which is described in FIG. 7.

The search for occurrences as rare as fetal cells or micrometastases involves extreme quality and efficacy of all the process stages. First of all, the antibodies must be very effective in order to ensure a good recovery of the cells sought. Cellular losses at the time of rinsing and recovery manipulations must be avoided. It likewise is necessary to reduce to the extent possible false positives resulting from non-specific cells, but also from colorant crystals and miscellaneous residues which under fluorescence may be confused with cells.

Image analysis is capable of resolving certain differentiations. Nonetheless, in the case of rare elements on the order of 1 to 50 cells per sample, the total artifact number should be below these values, which requires high performances in the marked-cell and unmarked-cell separation chain, and a high quality in cell recovery. The customary procedures of collection on a slide and staining generate a "noise" which is not compatible with such requirements.

On the other hand, the filtration apparatus according to the invention makes it possible to meet these requirements. It consists of a component (41) of molded silicone, for one-time use. This component (41) has a thickness on the order of 2 millimeters and has twelve projections (51) with a diameter of 6 millimeters and a height of 10 millimeters. These projections (51), normally closed, may be perforated by a hollow needle (48) provided at the end of the separator tube (42).

The silicone component (41) is positioned in a rigid perforated plate (43). The perforations are arranged in a manner complementary to the projections (51) of the component (41). This plate (43) may be connected imperviously to a holder (45) and maintained in position by clamps (44). A toric joint completes the imperviousness of this joining. The holder (45) also has perforations arranged opposite the perforations of the plate (43). The holder is connected to a depression source. A microporous filtration membrane (47) is arranged between the plate (43) and the holder (45). It advantageously involves a polycarbonate microporous membrane the alveoli of which have a 2-micron section.

The functioning of this filtration module is as follows:

The component (41) is delivered with a protective film placed under the lower side. One or several projections may be opened. The plate (41) is placed on the holder (43) after the microporous membrane has been positioned, and the whole is locked with clamps (44).

The separation tube (2) is delivered with a protective hood which avoids any contamination. This hood is removed and one of the projections of the component (41) is perforated.

At the time of collection of the rosettes deriving from the separator, the isolated paramagnetic particles pass through the membrane, while the rosettes remain on the surface. The porosity of the microporous membrane allows passage of the paramagnetic particles the section of which is on the order of a micron, but not the rosettes, the section of which is on the order of 5 microns.

For the collection of nuclei, in the absence of balls, the porosity may be 1 to 2 microns.

The staining may be performed prior to the filtration with fluorescent dyes of the IP or BET type (non-commercial) or else by staining on the filter after the latter has been extracted from the retention system.

The combination of a separator apparatus consisting of a tube with a section very much less than the length placed in a magnetic field gradient, and a filtration system such as described above, offers numerous advantages. First of all, such a combination facilitates automation of biological analysis. It also makes it possible to undertake analyses and applications for therapeutic purposes requiring a high degree of sterility. The paramagnetic balls make possible a sorting of the cells, and in particular a separation of the sought cells and the other cells. The filter makes it possible to eliminate certain surplus cells, such as platelets, as well as the surplus paramagnetic balls. The filter also has the function of concentration of the rare calls sought over a reduced surface, facilitating analysis by imagery. This filter also makes it possible, in particular for therapeutic applications, to undertake a culture of the sought cells. For this purpose, the filter serves as a holder for the cells and may be provided with a nutritive liquid suitable for promoting cellular multiplication.

The invention will be understood better in the preceding, by way of non-limiting example.

What is claimed is:

1. A process for separating cells, comprising:

contacting a sample containing (1) target cells which are affixed to paramagnetic balls, (2) free cells, and (3) surplus paramagnetic balls, with a nonhomogeneous magnetic field, wherein, during the contacting, the sample is circulated in a tube, wherein the nonhomogeneous magnetic field is applied over a section of the tube measuring less than the length of the tube, and wherein the tube has a proximal portion and a distal portion with respect to fluid flow in the tube, wherein the surplus paramagnetic balls are immobilized in the proximal portion of the tube and the target cells which are affixed to paramagnetic balls are immobilized in the distal portion of the tube.

2. The process of claim 1, wherein the free cells pass through the tube.

3. The process of claim 1, further comprising contacting cells with paramagnetic balls, wherein the paramagnetic balls are derivatized with a substance capable of binding specifically to a complementary substance on the target cells.

4. The process of claim 1, wherein the target cells are bacteria, fetal cells, stock cells of bone marrow or circulating cancerous cells.

5. The process of claim 1, wherein the sample is circulated in a tube coiled into a spiral in a magnetic-field gradient.

6. The process of claim 1, wherein the section of the tube ranges between 0.5 and 3 millimeters.

7. The process of claim 1, wherein the length of the tube is greater than 10 centimeters.

8. The process of claim 1, wherein the sample is introduced, prior to circulation in the tube, into a reservoir connected to the tube, wherein the reservoir is raised in relation to the tube to provide circulation of the sample by gravity.

9. The process of claim 8, wherein a first volume of sample and a second volume of a rinse liquid are introduced into the reservoir without mixing and without interface layer.

10. The process of claim 1, wherein the preparation is aspirated into the tube placed in the magnetic field gradient, wherein the lower end of the tube is connected to a peristaltic pump.

11. The process of claim 1, wherein magnets which produce the magnetic field are mobile in relation to the tube.

12. The process of claim 1, wherein sample and, optionally, reagents used for the separation, flow in continuous manner in tube at a speed ranging between 0.1 and 10 cm/s.

13. The process of claim 1, further comprising filtering the target cells which are affixed to paramagnetic balls with a microporous membrane filter having a porosity which is greater than the diameter of the paramagnetic balls and less than the diameter of the affixed cells.

14. The process of claim 1, wherein a subsequent filtration stage is undertaken with the aid of a microporous membrane filter the porosity of which is greater than the diameter of the paramagnetic balls and certain surplus cells, and less than the diameter of the affixed cells.

* * * * *

UNITED STATES PATENT AND TRADEMARK OFFICE
CERTIFICATE OF CORRECTION

PATENT NO. : 6,143,577
DATED : November 7, 2000
INVENTOR(S) : Jean-Claude Bisconte De Saint Julien It is certified that error appears in the above-identified patent and that said Letters Patent is hereby corrected as shown below:

On the title page, Item [19], and Item [75], the Inventor's name are listed incorrectly. Items [19] and [75] should read as follows:

[19]  Bisconte De Saint Julien

[75]  Inventor:  Jean-Claude Bisconte De Saint Julien, Briis sous Forges, France Signed and Sealed this Nineteenth Day of June, 2001

*Attest:*

NICHOLAS P. GODICI
*Attesting Officer*   Acting Director of the United States Patent and Trademark Office